US008759258B2

(12) United States Patent
Al-Murrani et al.

(10) Patent No.: US 8,759,258 B2
(45) Date of Patent: Jun. 24, 2014

(54) METHODS AND COMPOSITIONS FOR DIAGNOSING OSTEOARTHRITIS IN A FELINE

(75) Inventors: Samer Waleed Khedheyer Al-Murrani, Topeka, KS (US); William David Schoenherr, Hoyt, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 1133 days.

(21) Appl. No.: 12/600,064

(22) PCT Filed: May 1, 2008

(86) PCT No.: PCT/US2008/062225
§ 371 (c)(1),
(2), (4) Date: Sep. 10, 2010

(87) PCT Pub. No.: WO2008/137549
PCT Pub. Date: Nov. 13, 2008

(65) Prior Publication Data
US 2010/0323908 A1    Dec. 23, 2010

Related U.S. Application Data

(60) Provisional application No. 60/927,167, filed on May 1, 2007.

(51) Int. Cl.
  *C40B 30/04* (2006.01)
(52) U.S. Cl.
  USPC .......................................................... 506/9
(58) Field of Classification Search
  None
  See application file for complete search history.

(56) References Cited

U.S. PATENT DOCUMENTS

| 4,376,110 A | 3/1983 | David et al. |
| 4,843,155 A | 6/1989 | Chomczynski |
| 4,946,778 A | 8/1990 | Ladner et al. |
| 5,530,101 A | 6/1996 | Queen et al. |
| 5,545,580 A | 8/1996 | Sheng et al. |
| 5,569,825 A | 10/1996 | Lonberg et al. |
| 5,585,089 A | 12/1996 | Queen et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,693,761 A | 12/1997 | Queen et al. |
| 5,693,762 A | 12/1997 | Queen et al. |
| 5,770,429 A | 6/1998 | Lonberg et al. |
| 5,789,650 A | 8/1998 | Lonberg et al. |

(Continued)

FOREIGN PATENT DOCUMENTS

| EP | 1780276 | 5/2007 |
| JP | 2004-279334 A | 10/2004 |

(Continued)

OTHER PUBLICATIONS

Simonaro et al. (May 2005) Pediatric Research vol. 57 pp. 701 to 707.*

(Continued)

*Primary Examiner* — Christian Boesen
(74) *Attorney, Agent, or Firm* — Thomas M. Hunter

(57) ABSTRACT

Methods, compositions and kits for diagnosing osteoarthritis in a feline are disclosed. The methods of the invention comprise detecting differential expression of at least one biomarker in a body sample. preferably a blood sample, where the biomarker is differentially expressed in osteoarthritis.

14 Claims, 4 Drawing Sheets

(56) References Cited

U.S. PATENT DOCUMENTS

| | | | |
|---|---|---|---|
| 5,910,771 | A | 6/1999 | Stumberg et al. |
| 5,932,448 | A | 8/1999 | Tso et al. |
| 7,065,236 | B2 | 6/2006 | Marcelpoli et al. |
| 2003/0054426 | A1 | 3/2003 | Welsch |
| 2005/0118625 | A1 | 6/2005 | Mounts |
| 2005/0221383 | A1 | 10/2005 | Liew et al. |
| 2006/0263797 | A1 | 11/2006 | Liew et al. |

FOREIGN PATENT DOCUMENTS

| | | |
|---|---|---|
| JP | 2006-505555 A | 2/2006 |
| JP | 2008-510168 A | 4/2008 |
| WO | 0120018 A | 3/2001 |
| WO | WO 01/053531 | 7/2001 |
| WO | 2006014013 A | 2/2006 |
| WO | WO 2006/074089 | 7/2006 |
| WO | 2006138646 A | 12/2006 |
| WO | WO 2007/002837 | 1/2007 |

OTHER PUBLICATIONS

NCBI 12 15 2015 XM_849889 (downloaded Dec. 15, 2012) main page of obsolete PREDICTED_*Canis lupus* familiaris secreted protein, acidic, cysteine-r - Nuc pp. 1 to 3.*
NCBI 12 15 2015 XM_849889.2 (downloaded Dec. 15, 2012) sequence page of obsolete PREDICTED_*Canis lupus* familiaris secreted protein, acidic, cysteine-r - Nuc pp. 1 to 5.*
Lockhart et al. (Dec. 1996) Nature Biotechnology vol. 14 pp. 1675 to 1680.*
Sippl et al. (Jan. 2, 2008) Bioinformatics vol. 24 pp. 426 to 427.*
Barany, 1991, "Genetic disease detection and DNA amplification using cloned thermostable ligase," PNAS 88(1):189-193.
Beale, 2004, "Use of Nutraceuticals and Chondroprotectants in Osteoarthritic Dogs and Cats," Veterinary Clinics Small Animal Practice 34(1):271-289.
Bird, 1988, "Single-Chain Antigen-Binding Proteins," Science 242(4877):423-426.
Clarke et al., 2005, "Prevalence of Radiographic Signs of Degenerative Joint Disease in a Hospital Population of Cats," Veterinary Record 157(25):793-799.
Clarke et al., 2006, "Feline Osteoarthritis: A Prospective Study of 28 Cases," J. Small Animal Practice 47(8):439-445.
Cole et al., 1985, *Monoclonal Antibodies and Cancer Therapy* Alan R. Liss, Inc., pp. 77-96.
Cote et al., 1983, "Generation of human monoclonal antibodies reactive with cellular antigens," PNAS 80(7):2026-2030.
Godfrey, 2005, "Osteoarthritis in Cats: A Retrospective Study," J. Small Animal Practice 46(9):425-429.
Guatelli et al., 1990, "Isothermal, in vitro amplification of nucleic acids by a multienzyme reaction modeled after retroviral replication," PNAS 87(5):1874-1878.
Hardie, 1997, "Management of Osteoarthritis in Cats," Veterinary Clinics of North America: Small Animal Practice 27(4):945-953.
Huse, 1989, "Generation of a large combinatorial library of the immunoglobulin repertoire in phage lambda," Science 246(4935):1275-1281.

Huston et al., 1988, "Protein engineering of antibody binding sites: recovery of specific activity in an anti-digoxin single-chain Fv analogue produced in *Escherichia coli*," PNAS 85(16):5879-5883.
International Search Report and Written Opinion in International Application No. PCT/US08/062225, mailed Mar. 4, 2009.
Kim et al., 2006, "The Catabolic Pathway Mediated by Toll-like Receptors in Human Osteoarthritic Chondrocytes," Arthritis and Rheumatism 54(7):2152-2163.
Kohler et al., 1975, "Continuous cultures of fused cells secreting antibody of predefined specificity," Nature 256(5517):495-497.
Kozbor et al., 1983, "The Production of Monoclonal Antibodies from Human Lymphocytes," Immunology Today 4(3):72-79.
Kwoh et al., 1989, "Transcription-based amplification system and detection of amplified human immunodeficiency virus type 1 with a bead-based sandwich hybridization format," PNAS 86(4):1173-1177.
Lizardi P.M. et al., 1988, "Exponential amplification of recombinant-RNA hybridization probes," Biotechnology 6:1197-1202.
Morrison et al., 1984, "Chimeric human antibody molecules: mouse antigen-binding domains with human constant region domains," PNAS 81(21):6851-6855.
Nakamura et al., 1996, "Enhancement of PSARC (Osteonectin) Synthesis in Arthritic Cartilage," Arthritis and Rheumatism 39(4):539-551.
Neuberger et al., 1984, "Recombinant antibodies possessing novel effector functions," Nature 312:604-308.
Partial International Search Report in International Application No. PCT/US08/062225, mailed Dec. 18, 2008.
Reeck et al., 1987, "'Homology' in proteins and nucleic acids: a terminology muddle and a way out of it," Cell 50(5):667.
Takeda et al., 1985, "Construction of chimaeric processed immunoglobulin genes containing mouse variable and human constant region sequences," Nature 314(6010):452-454.
Ward et al., 1989, "Binding activities of a repertoire of single immunoglobulin variable domains secreted from *Escherichia coli*," Nature 341(6242):544-546.
Zapata et al., 1995, "Engineering linear F(ab')2 fragments for efficient production in *Escherichia coli* and enhanced antiproliferative activity," Protein Engineering 8(10):1057-1062.
Bluteau G et al.: "Differential Gene Expression Analysis in a Rabbit Model of Osteoarthritis induced by Anterior Cruciate Ligament (ACL) Section," Biorheology, Elseview Science Ltd. (Jan. 1, 2002), pp, 247-259 39:1/02 Oxford, GB.
Database NCBI Nucleotides [Online] NCBI, 2005, "*Canis familiaris* similar to SPARC precursor (Secreted protein acidic and rich in cysteine) (Osteonectin) (ON) (Basement-membrane protein 40) (BM-40) (LOC612159), mRNA," Abstract An: XM_849889.
Database NCBI Nucleotides [Online] NCBI; 2008, "*Felis catus* mRNA for TCR Alpha Constant Chain, Partial cds," GenBank AN: D89022.1.
Database NCBI Nucleotides [Online] NCBI; 2005, "*Felis catus* Toll-like Receptor 2 mRNA, Partial cds," GenBank AN: AY700369.1.
Database NCBI Nucleotides [Online] NCBI; 2005, "Predicted: *Canis familiaris* Similar to ATP-Binding Cassette, Sub-Family A, Member 5, Transcript Variant 6 (LOC480455), mRNA," NCBI Reference Sequence AN: XM_857754.1.

* cited by examiner

| Top-Blast-Annot | Top-Match% | P-value | Mean-Ratio | Fold-Change | Top-Accn | Hum-Annot | Hum-Id | Hum-Match% |
|---|---|---|---|---|---|---|---|---|
| PREDICTED: Canis familiaris similar to SPARC precursor (Secreted protein acidic and rich in cysteine) (Osteonectin) (ON) (Basement-membrane protein 40) (BM-40) (LOC612159), mRNA | 75.474957 | 6.00E-06 | 7.39773 | 7.39773 | XM_849989 (SEQ ID NO. 4) | Macaca fascicularis brain cDNA, clone: QccE-10162; similar to human secreted protein, acidic, cysteine-rich (osteonectin)(SPARC), mRNA, RefSeq: NM_003118.1 | AB169483 | 72.02073 |
| PREDICTED: Canis familiaris similar to interferon-induced protein with tetratricopeptide repeats 5 (IFIT-5) (Retinoic acid- and interferon-inducible 58 kDa protein) (LOC486788); mRNA | 95.559849 | 0.000495269 | 3.37984 | 3.37984 | XM_543917 | Homo sapiens interferon-induced protein with tetratricopeptide repeats 5 (IFIT5), mRNA >gi|11445109|gb|U34605.1|HSU34605 Human retinoic acid- and interferon-inducible 58K protein RI58 mRNA, complete cds | NM_012420 | 92.27799 |
| Canis familiaris lectin, galactoside-binding, soluble, 9 (galectin 9) (LGALS9), mRNA >gi|46102472|gb|AY521549.1| Canis familiaris galectin 9 (LAT) mRNA, complete cds | 85.17179 | 0.000014001 | 2.00711 | 2.00711 | NM_001003345 | Homo sapiens lectin, galactoside-binding, soluble, 9 (LGALS9), transcript variant short, mRNA | NM_002308 | 76.1302 |
| PREDICTED: Pan troglodytes hypothetical LOC465771, transcript variant 4 (LOC465771), mRNA | 89.835972 | 0.000918909 | 0.498995 | -2.00403 | XM_521189 | Homo sapiens G protein-coupled receptor associated sorting protein 2, mRNA (cDNA clone IMAGE:5271751) | BC025707 | 89.83957 |
| PREDICTED: Canis familiaris similar to Dickkopf related protein-3 precursor (Dkk-3) (Dickkopf-3) (hDkk-3) (LOC478857), mRNA | 77.099237 | 0.000232116 | 0.474832 | -2.10605 | XM_534060 | Homo sapiens dickkopf-3 (DKK-3) mRNA, complete cds | AF177396 | 31.48855 |
| PREDICTED: Canis familiaris similar to Tetraspanin-13 (Tspan-13) (Transmembrane 4 superfamily member 13) (Tetraspan NET-6) (LOC482332), mRNA | 89.830508 | 0.000861772 | 0.471024 | -2.12304 | XM_539449 | full-length cDNA clone CS0DI065YG03 of Placenta Cot 25-normalized of Homo sapiens (human) | CR602288 | 50.84745 |
| PREDICTED: Pan troglodytes similar to cytokeratin 18 (424 AA) (LOC451924), mRNA | 67.234043 | 0.000334521 | 0.397539 | -2.51548 | XR_025356 | Homo sapiens BAC clone RP11-357C22 from Y, complete sequence | AC012657 | 57.23404 | p value < 0.001 FC > 2.0

FIGURE 1

| Top-Blast-Annot | Top-Match% | p-value | Mean-Ratio | Fold-Change | Top-Accn | Hum-Annot | Hum-Id | Hum-Match% |
|---|---|---|---|---|---|---|---|---|
| PREDICTED: Canis familiaris similar to WW domain binding protein 2; transcript variant 2 (LOC484477), mRNA | 95.777351 | 0.000421314 | 1.999 | 1.999 | XM_844270 | Synthetic construct Homo sapiens clone FLH168662_01X, RZPDo834D1234D WBP2 mRNA, complete sequence | DQ891052 | 92.89827 |
| PREDICTED: Canis familiaris similar to Galectin-3 binding protein precursor (Lectin galactoside-binding soluble 3 binding protein) (Mac-2 binding protein) (Mac-2 BP) (MAC2BP) (Tumor-associated antigen 90K) (LOC483345), mRNA | 46.318868 | 0.000788614 | 1.85093 | 1.85093 | XM_540464 | Homo sapiens clone FLH184271_01L, RZPDo839E011430 LGALS3BP mRNA, partial cds | DQ895424 | 43.17757 |
| Felis catus Toll-like receptor 2 mRNA, partial cds | 100 | 0.000391666 | 1.79388 | 1.79388 | AY700269 (SEQ ID NO. 2) | Homo sapiens clone FLH169452_01L, RZPDo839D01850 TLR2 mRNA, partial sequence | DQ894005 | 84.53782 |
| PREDICTED: Canis familiaris similar to uridine phosphorylase 1 (LOC480772), mRNA | 85.587771 | 0.000366772 | 1.7344 | 1.7344 | XM_537869 | NULL | NULL | NA |
| PREDICTED: Canis familiaris similar to monoacylglycerol O-acyltransferase 1 (LOC485548), mRNA | 54.786031 | 0.000815306 | 1.71051 | 1.71051 | XM_545037 | Homo sapiens monoacylglycerol O-acyltransferase 1 (MOGAT1) mRNA >gi|15099856|gb|AF384163.1|AF384163 Homo sapiens diacylglycerol acyltransferase 2-like protein mRNA, complete cds | XM_053185 | 48.87348 |
| Synthetic construct Homo sapiens clone FLH189257_01X; RZPDo839Q0374D PKM2 mRNA, complete sequence | 97.790055 | 0.000488898 | 1.62476 | 1.62476 | DQ892739 | Synthetic construct Homo sapiens clone FLH189257_01X, RZPDo839Q0374D PKM2 mRNA, complete sequence | DQ892739 | 97.79005 |
| Homo sapiens WD repeat and FYVE domain containing 3 (WDFY3); transcript variant 1 mRNA | 43.818182 | 0.0031426 | 1.55407 | 1.55407 | NM_014991 | Homo sapiens mRNA for KIAA0993 protein, partial cds | AB023210 | 43.81818 |
| PREDICTED: Canis familiaris similar to RAB6 interacting protein 1 (LOC478644), mRNA | 95.789474 | 0.0007268 | 1.5436 | 1.5436 | XM_534048 | Homo sapiens RAB6 interacting protein 1 (RAB6IP1), mRNA | NM_015213 | 95.78947 |
| PREDICTED: Canis familiaris similar to Coronin-1C (Coronin-3) (hCRNN4) (LOC480318), mRNA | 86.579923 | 0.000634806 | 1.53908 | 1.53908 | XM_543444 | Homo sapiens coronin, actin binding protein, 1C (CORO1C), mRNA | NM_014325 | 84.76703 |
| Mus musculus cDNA; RIKEN full-length enriched library, clone:M2C1002E14 product:588-11244 binding protein, full insert sequence | 41.078838 | 0.000244756 | 0.665385 | 0.66184 | NM_133352 | NULL | NULL | NA |
| PREDICTED: Canis familiaris similar to Hypothetical UPF0394 protein ZK1128.2 in chromosome III; transcript variant 2 (LOC480655), mRNA | 80.599395 | 0.000365505 | 0.680749 | 1.51344 | XM_863412 | Macaca fascicularis testis cDNA clone QtsA-10049, similar to human hypothetical protein MGC3329 (MGC3329), mRNA, RefSeq | AB168137 | 85.6543 |

FIGURE 2A

| | | | | | |
|---|---|---|---|---|---|
| PREDICTED: Canis familiaris similar to reticulocalbin 2 (LOC487665), mRNA | 94.830893 | 0.000493882 | 0.686019 | 1.61472 | XM_544790 | NM_024486.2 full-length cDNA clone CS0CAP049YK06 of Placenta Cot 25-normalized of Homo sapiens (human). | 90.81452 |
| PREDICTED: Canis familiaris similar to RAB GTPase activating protein 1-like; transcript variant 2 (LOC480054), mRNA | 34.863946 | 0.000593008 | 0.658626 | 1.525526 | XM_856054 | Human DNA sequence from clone RP1-102G20 on chromosome 1q24-25 Contains a novel pseudogene, two novel genes, a ribosomal protein S26 (RPS26) pseudogenes; the 3-prime end of the gene for expressed in hematopoietic cells (heart, liver) (HLL), the gene for Siah-interacting protein (SIP); the 3-prime end of the MRPS14 gene for mitochondrial ribosomal protein S14 and a CpG island. complete sequence. | 33.84354 |
| PREDICTED: Canis familiaris similar to ATP-binding cassette, sub-family A, member 6, transcript variant 1 (LOC480454), mRNA | 91.588765 | 0.000204232 | 0.65393 | 1.42924 | XM_857754 (SEQ ID NO. 11) | Homo sapiens mRNA for KIAA1608 protein, partial cds | 89.01869 |
| Felis catus CD7 antigen (CD7), mRNA >gi|49322600|dbj|AB154850.1| Felis catus fCD7 mRNA for feline CD7, complete cds | 100 | 2.48E-05 | 0.647573 | 1.54423 | NM_001009293 | Homo sapiens clone FLH137866.01L RZPDo839D122149D CD7 mRNA, partial sequence | 15.71125 |
| PREDICTED: Canis familiaris similar to basic leucine zipper and W2 domains 2, transcript variant 1 (LOC475250), mRNA | 96.930946 | 0.000283223 | 0.626615 | -1.5908 | XM_532484 | Homo sapiens clone FLH196853.01L RZPDo839B03262D BZW2 mRNA, partial sequence | 95.39642 |
| Felis catus BCL2B-cell CLL/lymphoma 2 (BCL2), mRNA >gi|25186510|dbj|AB096611.1| Felis catus mRNA for bcl-2 protein, complete cds | 86.222222 | 0.0003K0779 | 0.626335 | 1.59914 | NM_001003340 | Homo sapiens B-cell CLL/lymphoma 2 (BCL2); nuclear gene encoding mitochondrial protein, transcript variant alpha, mRNA | 79.77778 |
| PREDICTED: Canis familiaris similar to Selenoprotein P precursor (SeP); transcript variant 1 (LOC479346), mRNA | 46.238085 | 0.000143766 | 0.624247 | 1.60193 | XM_862927 | Homo sapiens selenoprotein P, plasma, 1 (SEPP1), mRNA | 24.52381 |
| PREDICTED: Canis familiaris similar to SH3 domain-binding protein 5 (SH3 domain-binding protein that preferentially associates with BTK) (LOC485657), mRNA | 93.691589 | 0.000143766 | 0.621661 | 1.60859 | XM_542777 | Synthetic construct Homo sapiens clone FLH190536.01X, RZPDo8389B05768D SH3BP5 mRNA, complete sequence | 91.35514 |
| Homo sapiens PC4 and SFRS1 interacting protein 1 (PSIP1), transcript variant 2, mRNA >gi|3283336|gb|AF063020.1|AF063020 Homo sapiens lens epithelium-derived | 85.310925 | 0.000020451 | 0.604892 | 1.65319 | NM_033222 | Homo sapiens lens epithelium-derived growth factor gene, alternatively spliced; complete cds | 86.31091 |

FIGURE 2B

| | | | | | |
|---|---|---|---|---|---|
| growth factor mRNA, complete cds | | | | | |
| Homo sapiens zinc finger protein 642 (ZNF642); mRNA | 54.51448 | 0.000270517 | 0.604648 | 1.65285 | XM_595813 | Human DNA sequence from clone RP11-636D10 on chromosome 1 Contains the gene for a novel zinc finger protein, the gene for a novel protein and three novel genes; complete sequence | AL603639 | 54.51448 |
| PREDICTED: Canis familiaris similar to Zinc finger protein 292 (LOC481908); mRNA | 96.801942 | 0.000810683 | 0.602343 | 1.66018 | XM_538029 | PREDICTED: Homo sapiens zinc finger protein 292, transcript variant 4 (ZNF292); mRNA | XM_938663 | 93.93224 |
| Felis catus CD3 antigen epsilon (CD3E); mRNA >gi|5637811|dbj|AB193840.1| Felis catus cd3e mRNA for CD3 antigen epsilon subunit, complete cds, cell_type:thymocyte | 83.159722 | 0.000681424 | 0.590272 | 1.69413 | NM_001009862 | NULL | NULL | NA |
| PREDICTED: Canis familiaris similar to Protein C22orf8 (LOC481208); mRNA | 48.101266 | 0.000747509 | 0.57799 | 1.73013 | XM_538329 | Homo sapiens family with sequence similarity 118, member A; mRNA (cDNA clone MGC:3848 IMAGE:3863684); complete cds | BC013696 | 64.48463 |
| PREDICTED: Canis familiaris similar to Nonhistone chromosomal protein HMG-14 (High-mobility group nucleosome binding domain 1); transcript variant 2 (LOC608119); mRNA | 93.735499 | 0.000294192 | 0.577286 | 1.73224 | XM_844714 | PREDICTED: Homo sapiens similar to Nonhistone chromosomal protein HMG-14 (High-mobility group nucleosome-binding domain-containing protein 1) (LOC728851), mRNA | XM_001132791 | 65.89327 |
| Felis catus mRNA for TCR alpha constant chain, partial cds | 100 | 8.11E-05 | 0.57407 | 1.74195 | DB9022 (SEQ ID NO. 3) | NULL | NULL | NA |
| PREDICTED: Canis familiaris similar to DNA-binding protein SATB1 (Special AT-rich sequence binding protein 1) (LOC485550); mRNA | 98.860499 | 0.000107709 | 0.542275 | 1.84408 | XM_542770 | NULL | NULL | NA |
| PREDICTED: Pan troglodytes similar to profilin IIa (LOC480989); mRNA | 97.336362 | 0.000032347 | 0.540383 | 1.85054 | XM_516998 | Homo sapiens profilin 2 (PFN2), transcript variant 1; mRNA | NM_053024 | 97.33646 |
| p value < 0.001 FC >1.5 | | | | | |

```
                              SEQUENCE LISTING

<160> NUMBER OF SEQ ID NOS: 4

<210> SEQ ID NO 1
<211> LENGTH: 1384
<212> TYPE: DNA
<213> ORGANISM: Felis catus

<400> SEQUENCE: 1
tgacaatgtt taatgacagt gactatgtgt ccgctgctcc ccatagtgca gctttaaatg      60
tgatgtattc agaacaggac tatgttttta cagctgtttt caacagtact atggtttgtt     120
ctttacctgt attgatgaat attattagta attattatct ttaccattta aatgtgactg     180
aaagcatcca ggtttggaat actccattct ttcaagaaat tacagacatc gttttaaaa     240 ttgagctgta tttccaagca gctttgcttg gaatcattgt gactgcaatg ccaccttact     300
ttgccatgga aaatgcagag aatcataaga tcaaagctta tactcaactt aaactttcag     360
ggcttttacc gtctgcatat tggattggac aagctattgt tgatatcccc atattttttc     420
ttgttcttat tttgatgcta ggaagtttat ttgcatttca ttatggatta tatttttatg     480
ctataaagtt cctttctgtg gttttttgcc ttattggtta tgttccatca gtcattctgt     540
ttacctatgt tacttctttc actttcaaaa aaattttgaa taccaaagag ttttggtcat     600 ttattattc tgtgacagca ttggcttgca ttgcagtcac tgaaatcacg ttctttatgg     660
gatacacagt tacggctgtt ctccattata cctttgtat ggccattcca atctatccac     720
ttctaggttg tctgatttgt ttcataaaga tttcttggaa gaatattcga aaaaacgagg     780
acacgtataa tccatgggat agactttgg tggcagttat atcgccttac ctgcagtgtg     840
tactgtggat tttcctctta cagtactacg agaaaaaata cggaggcagg tcgatacgaa     900
aggatccctt tttcaggacc ctttcaacaa agtccaaaaa taggaagtct ccagaaccac     960
caaacaatga ggatgaagat gaagatgtca aagctgaaag actgaaggtc aaagagctaa    1020
tgagttgcca gtgttgtgag gagaaaccag ccattatggt cagctgtttg cataaagaat    1080
atgatgacaa gaaagatttt cttcttacaa gaaaagtaaa gaaagtagca actaaatatg    1140
tctctttctg tgtgaaaaaa ggagagatct tggggctact gggtccaaac ggtgcaggca    1200
aaagcacaat tatcaatatt ctggttggtg acattgaacc aacttcaggc caggtatttc    1260
taggaaatta ttcttcagaa ccaactgaag atgatgattt catttaatta tatggggata    1320
ctgtccttca aataacccca ctgggggcca gactttacat ttgcagggac aattttttgaa    1380 attt                                                                 1384

<210> SEQ ID NO 2
<211> LENGTH: 787
<212> TYPE: DNA
<213> ORGANISM: Felis catus
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (22)..(45)
<223> OTHER INFORMATION: n is a, c, g, or t

<400> SEQUENCE: 2
```

```
nnaaaaagca tggactatga cnnnnnnnnn nnnnnnnnnn nnnnngtatt cacttacaga    60
aagagttaaa agagtcacag tagaaagcag taaggtgttt ctggttcctt gtttactttc   120
acaacattta aaatcattag aatatttgga tctcagtgac aatttaatgg ttgaagaata   180
cttgagaaat gccgcctgtg agcatgcctg ccccctccta caaaccttaa ttttaaggca   240
aaatcgtttg aaatcattag aaaaaaccgg agaaactttg cttactctga aaaacttgat   300
taaccttgat attagtaaga acagttatct ttctatgcct gaaacttgtc agtggccaga   360
aaagttgaaa tatttgaact tatccaacac cagaatatac agcttaaccc gatgcatccc   420
ctggacactg gaaattttag atattagcaa taacaatctc gattcatttt ctctgacttt   480
gccacaactc aaagaacttt atatttccag aaataagttg aagactctac cagatgcctc   540
cttcttaccc acgttacagg tcatgagaat cagcagaaat gcaataaaca ctttctcgaa   600
ggagcaactt gattcttttc aaagactgac gactttggaa gctggcggca acaatttcat   660
ttgctcctgt gattcctgtc tttccgcggg agcagcagca ctggcccaga tcctgacgac   720
tggcagacat tactgtgtga ctctcatctc gtgcggggca gcggtcagac acctctccag   780
ctctgag                                                            787

<210> SEQ ID NO 3
<211> LENGTH: 922
<212> TYPE: DNA
<213> ORGANISM: Felis catus
<220> FEATURE:
<221> NAME/KEY: misc_feature
<222> LOCATION: (11)..(44)
<223> OTHER INFORMATION: n is a, c, g, or t

<400> SEQUENCE: 3
gggtgaacta nnnnnnnnnn nnnnnnnnnn nnnnnnnnnn nnnngtggta ctcttgatgc    60
ttggacaaac ccacggagac tcagtgaccc agatggaagg cccagtgacc ctctccaaag   120
gggagtccct gactataaac tgtacttatt cagcgacagg gtaccccact cttttctggt   180
atgtccagta tcctggagaa ggtccacagc tcctcctgaa agccttgagg gacaaggaga   240
agggaagtca caaaggtttt gaagccacct acgatggaaa atccaaaacc ttccacttgg   300
tgaaatcatt agtgcaagcg tcagattcag ctgtgtacta ctgtgctgcg agtgatcacg   360
gcacgcttat cttttggaaag ggcacaagac tttctgtgat tgcaactatt cagaaccctg   420
accctgccgt gtaccagctg aaaagccctg aatccagtaa catctctgtc tgcctgttca   480
ctgattttga ttcggaagtc aatgtgaatc catccacaga gtccaacatg attagattga   540
aaagtacttc actggacatg aagactatgg attccaagag caacggggcc ctggcctgga   600
gcaacagctt tgatttggga tgcaacagta ccttcaacta caccttccac tccagctcag   660
agtttccctg cgatgccaat gtggtaaaga aaggctttga aacagatatg agcctaaatt   720
tcaacaacct gaccgtgatt cttgttccgc atcatcttcc ctaaagcggt tggcttttac   780
cctgctcatg aacccaaaac ctggggtcca gcctaaggtc cccaaaaaaa tgggaaaacc   840
caccccttcc cctgccccccc ccccccccct tccccccccct tttttaaaaa aaaaaaggcc   900
ccctccctct cccccccgg ga                                             922

<210> SEQ ID NO 4
<211> LENGTH: 1158
<212> TYPE: DNA
<213> ORGANISM: Felis catus
```

```
<400> SEQUENCE: 4
cgaacaggag gtggtggctg aaaacccctg ccagaaccac cactgcaaac atggcaaagt      60
gtgtgagctg gatgagaaca acacccccat gtgcgtgtgc caggaccota ccagctgccc     120 tgcccccatt ggcgagtttg agaaggtgtg cagcaatgac aacaagacct tcgactcttc     180
ctgccacttc tttgccacca agtgcaccct ggagggcacc aagaagggcc acaaactcca     240
cctggactac attgggcctt gcaaatacat cccccctgc ctggactccg agctgaccga      300 attcccctg cgcatgcggg actggctcaa gaacgtcctg gtcactctgt acgaaaggga      360
cgaggacaac aaccttctga ccgagaagca gaaactgcga gtgaagaaga tccatgagaa     420
cgagaagcgc ctggaggctg gagaccaccc cgtggagctg ctggcccggg acttcgagaa     480
gaactacaac atgtacatct tccccgtgca ttggcagttt ggccagctgg accagcaccc    540
cattgatggg tacctgtccc acacggagct ggccccactg cgtgcacccc tcatcccat     600 ggagcactgc accacccgct ttttgagac ctgcgacctg gacaatgaca agtacatcgc     660
cctggatgag tgggccggct gcttcggcat caaggagcag gatattgaca aggatctggt    720
gatctaaatc cacgcctgcc tccttccgca gttccggatc ctccctcttt gatcttcccc    780
ttcctgtttc ccccaaagtt taaaatgttt ggatggtttg ttgttctgcc tggggacaag    840
gtgctaatat agatttacac gaatacatta acggtgctac aaatggaaat tgtaacccaa    900
gtcgtgacat tcttaggtgt gactgctctc actgcctctt gctcgccac taacggcccc     960 gttttgctct cgccccttgc ggtgtccccc gttgtcttag tggcgtgtgg gtgggaactt   1020
tgatctgctc agcctgcctt caacacacat tgcgtcttca gattttccct ccttcctcgg   1080
tttggaacta acgctcacca ggggtagtct tggtgttcat tttatttcag ggtatgggct   1140 ggccggggg ggggggg                                                    1158
```

METHODS AND COMPOSITIONS FOR DIAGNOSING OSTEOARTHRITIS IN A FELINE

CROSS REFERENCE TO RELATED APPLICATIONS

This application is a U.S. filing under 35 USC 371 of International Application No. PCT/US2008/062775 filed on May 1, 2008, which claims the benefit of U.S. Provisional Application No. 60/927,167 filed on May 1, 2007. The above-cited applications are incorporated herein by reference in their entirety.

FIELD OF THE INVENTION

The present invention relates to the identification of novel osteoarthritic biomarkers in felines and diagnostic methods, compositions, and kits related thereto.

BACKGROUND OF THE INVENTION

Arthritis, more particularly osteoarthritis (OA), is a degenerative joint disease commonly occurring in humans and in companion animals. OA involves progressive deterioration of articular cartilage, with loss of proteoglycan and collagen and proliferation of new bone, accompanied by a variable inflammatory response within the synovial membrane. It is the most common form of joint and musculoskeletal disease affecting dogs, but cats may also suffer from this condition.

Feline OA is disease primarily affecting aged felines 10 years of age or older. Animals suffering from this disease characteristically jump less, reduce the height of their jumps or stop jumping entirely, avoid going up or down stairs, and tend to use their litter box less. Cats with OA also appear to be less friendly, exhibit changes in their sleep-wake patterns, and may have grooming problems. The management of OA in cats is similar to treatment regimens in other species which include environmental modification, treatment of obesity, controlled moderate exercise, pain control, and surgery.

Environmental modification begins with the placement of food bowls and litter pans in locations that do not require leaping or stair climbing. Small ramps can be built to a feeding station or into the litter box. The attempt is made by the pet owner to reduce large leaps up or down, to encourage moderate exercise, and to create an environment where the cat is not faced with an obstacle course to maintain a daily routine. Environmental modification does not slow the progression of the disease.

Overweight cats with OA can benefit from weight control. A reduction in body weight will alleviate the pressure and pain on the affected joint(s). Though weight loss in overweight or obese cats can help alleviate the pain caused by OA, it does not stop the progression of the disease.

Pain control in cats is a problem because drug regimens that are safe in other species are not necessarily safe in cats. Though many pharmaceutical companies are evaluating non-steroidal anti-inflammatory drugs (NSAIDs) in cats for treatment of pain, aspirin is the only NSAID for which a safe, chronic dose has been established in the cat. Corticosteroids have been used to alleviate pain and inflammation, but their use may cause progression of OA. NSAIDs may help alleviate pain but will not alter the progression of OA.

Nutraceuticals have been used to alleviate pain associated with OA in cats. Chondroitin sulfate and glucosamine HCl used in combination or separately have been used as a treatment regimen in cats. There are no published clinical studies that indicate these nutraceuticals alter the progression of OA. Recent data in humans indicates that chondroitin and glucosamine may help alleviate pain in humans with severe OA.

Although helpful in some respect to provide symptomatic relief, the approaches described above are not entirely successful in disease management, as they clearly do not treat the underlying pathology. Indeed, not only are improved treatment methods needed, but also improved methods to monitor the clinical progress of an animal with OA and even to diagnose an animal that has OA, and those that may be genetically predisposed to developing OA but do not as yet display any clinical signs of the disease. Currently, extensive radiographic tests must be carried out to confirm a diagnosis of OA in an animal and these tests are useful only to identify animals that have manifest joint and tissue damage. Thus, there is a need for a simple diagnostic test for detecting OA in felines, as well as improved methods for monitoring the clinical progress of an animal with OA.

BRIEF SUMMARY OF THE INVENTION

The current invention relates to the identification of novel biomarkers for OA in felines and methods for the detection of arthritic animals based on a characteristic pattern of gene expression for these OA biomarkers in vivo. Specifically, the methods of the invention comprise detecting differential expression, compared to a control expression level, of at least one biomarker, in a body sample, preferably a blood sample, wherein the detection of differential expression of said biomarker specifically identifies animals that have OA. Thus, the method relies on the detection of at least one biomarker that is differentially expressed in OA in comparison to cells from normal, or control, animals.

The biomarkers of the invention are proteins and/or nucleic acids that are differentially expressed in OA in felines. In one aspect, the biomarkers of particular interest include the biomarkers listed herein on FIGS. 1-7.

Biomarker expression can be assessed at the protein or nucleic acid level using various methods. Thus, in another aspect, the invention relates to methods that utilize antibodies to detect the expression of OA biomarker proteins in feline samples. In this aspect of the invention, at least one antibody directed to a specific OA biomarker of interest is used. In a further aspect, expression levels can also be detected by nucleic acid-based techniques, including, for example, hybridization, microarray technologies and RT-PCR, including quantitative RT-PCR. Mass spectrometry, fluorescence activated cell sorting (FACS) or Luminex Xmap® bead technology may also be used to detect expression levels at both the protein or nucleic acid level.

It is further contemplated herein that the methods of the present invention may be used in combination with traditional diagnostic techniques that are able to detect the physical and morphological characteristics of degenerative joint disease. Thus, for example, the characterization of differential expression in genes for OA biomarkers in cells obtained from a blood sample of an animal may be combined with conventional diagnostic (e.g., radiological) techniques in order to corroborate a diagnosis of OA.

In a further aspect, the invention relates to compositions comprising one or more nucleic acid probes that specifically hybridize to a nucleic acid, or fragment thereof, encoding an OA biomarker of the present invention.

In an additional aspect, the invention relates to compositions comprising antibodies that specifically bind to a polypeptide encoded by a gene of an OA biomarker of the present invention.

The invention also relates to kits to diagnose OA in a feline comprising components that can be used to detect expression of the OA biomarkers of the present invention, including, but not limited to, the compositions and microarrays described herein.

It is also contemplated herein that the present invention relates to the use of the OA biomarkers and compositions disclosed herein in methods to diagnose OA in a feline.

In another aspect, it is also contemplated herein that the invention relates to methods for identifying bioactive dietary components or other natural compounds (referred to hereafter as "components") that may be tested for an ability to treat or ameliorate osteoarthritis in a feline comprising: (a) contacting a cell capable of expressing an RNA or protein product of one or more OA biomarkers disclosed in FIGS. 1-7 with a test component: (b) determining the amount of said RNA and/or product produced in the cells contacted with the test component; and (c) comparing the amount of said RNA and/or protein product in the cells contacted with the test component to the amount of the same said RNA or protein product present in a corresponding control cell that has not been contacted with the test component; wherein if amount of the RNA or protein product is altered relative to the amount in the control, the component is identified as one to be tested for an ability to treat or ameliorate osteoarthritis in a feline.

BRIEF DESCRIPTION OF THE FIGURES

FIG. 1 discloses feline OA biomarkers identified based on a selection criteria wherein the p value <0.001 and expression levels display a fold change of >2.0. With regard to FIGS. 1-2C, where mean-ratio >1, the gene is up regulated in OA and equates to a positive fold change. In contrast, where mean-ratio <1, the gene is down regulated in OA animals and equates to a negative fold change.

FIGS. 2A-2C disclose feline OA biomarkers identified based on a selection criteria wherein the p value <0.001 and expression levels display a fold change of >1.5.

DETAILED DESCRIPTION OF THE INVENTION

The present invention provides compositions and methods for identifying or diagnosing osteoarthritis in felines. The methods comprise the detection of the differential expression of specific biomarkers that are either selectively over expressed or under expressed in osteoarthritis. In this way, the biomarkers of the invention are capable of distinguishing between animals that have OA and those that do not. It is also contemplated herein that it may be possible to identify those animals that may be predisposed to developing OA or those that have OA but have not yet manifested morphological or physical changes. Said methods for diagnosing osteoarthritis involve detecting the differential expression of at least one biomarker that is indicative of osteoarthritis in a tissue or body fluid sample from a feline. In particular embodiments, antibodies and immunocytochemistry techniques or nucleic acid probes and hybridization techniques are used to detect expression of the biomarker of interest. Kits for practicing the methods of the invention are further provided.

"Diagnosing osteoarthritis" is intended to include, for example, diagnosing or detecting the presence of OA or a genetic predisposition thereto, monitoring the progression of the disease, and effectiveness of therapeutic intervention, as well as identifying or detecting cells or samples that are indicative of osteoarthritis. The terms diagnosing, detecting, and identifying osteoarthritis are used interchangeably herein. By "osteoarthritis" is intended those conditions characterized by degeneration of articular cartilage on the ends of bones that forms the surface of the joints and which may include, in later stages, accompanying changes in surrounding tissue in and around joints, e.g., bone, muscle, ligaments, menisci and synovium. Such physical changes are manifested by pain, swelling, weakness and loss of joint function.

OA has been classified into various grades or stages. Stage 1 is characterized by changes in chondrocyte metabolism such that there is an increase in cartilage matrix destroying enzymes such as metalloproteases. Protease inhibitors are synthesized in insufficient levels to combat the breakdown of the cartilage matrix. Stage 2 is characterized by erosion of the cartilage surface which causes a detectable increase in levels of proteoglycan and collagen fragments in the synovial fluid. During stage 3, the synovium is chronically inflamed, as a result of the breakdown products of cartilage. Macrophages in the synovium produce cytokines which can damage cartilage by directly destroying tissue or stimulating the chondrocytes to produce more metalloproteinases. Pro-inflammatory molecules may also cause damage at this stage. The resulting damage to the joint triggers an increase in bone growth as the body attempts to stabilize the joint, thus changing the normal mechanical and architectural features of the joint.

As discussed above, it is contemplated that the methods of the present invention may permit the identification of felines that may be predisposed to developing OA in future. In these animals it is contemplated that the methods of the present invention may be particularly useful, since conventional methods that rely on morphological changes to joint tissue would not typically identify these patients as being in need of therapeutic intervention. Use of haplotype markers and single nucleotide polymorphisms (SNPs) of the OA biomarkers disclosed herein may be particularly useful in this regard. In these cases, prophylactic measures or other therapies may be started as a means to ward off the more debilitating symptoms or physical damage associated with the later stages of OA.

In addition, it is contemplated herein while the OA biomarkers disclosed herein may be useful to diagnose a feline with OA, the OA biomarkers may also be useful targets for therapeutic intervention. For example, it is contemplated herein that a therapeutic benefit may be achieved prior to the manifestation of pathological physical changes in a feline (or even after physical changes have occurred), by altering the expression of any one or more of the biomarkers described in FIGS. 1-2C provided herein, e.g., by decreasing expression levels of genes overexpressed in OA, and/or by increasing expression in genes that are underexpressed in OA. In the case of some biomarkers as described in detail in the Examples below, this may be achieved by administration of a formulation high in EPA and DHA to a feline in need thereof.

It is further contemplated herein that components that may be of use to treat or ameliorate OA in felines may be identified by exposing cells to test components in vitro and assaying for changes in gene expression of one or more of the OA biomarkers. Such in vitro assays are familiar to one of skill in the art and may be performed according to conventional methods. Primary cultures of feline cells may be used as well as cell lines isolated from different feline tissues such as, e.g., blood, kidney, brain, tongue or lung. Feline cells for in vitro analysis may be obtained commercially, e.g. from American Type Culture Collection (ATCC, Manassas, Va.). Candidate components which show potential to influence the expression of OA biomarkers can then be slated for further experimentation, including as components of pet food formulations such as described in the Examples below.

While not intending to be limited to a particular mechanism, it is contemplated herein that the genotypic fingerprint of osteoarthritis in felines may be characterized by the differential expression of discrete genes, or biomarkers. The use of these molecular biomarkers of OA in molecular diagnostic assay formats can improve the detection of OA compared to current methods. Thus, in particular embodiments, a method for diagnosing osteoarthritis comprises detecting differential expression of a biomarker, wherein differential expression of the biomarker may be indicative of a disruption in a biochemical pathway related to or associated with OA. e.g., either as cause or effect. In still other embodiments, the methods comprise detecting differential expression of one or more OA biomarkers, e.g., a subset of biomarkers provided herein on FIGS. 1-2C. In this way, the methods of the present invention may not only permit the identification of an animal with osteoarthritis, but may also allow identification of an animal who may be genetically predisposed to developing OA.

The methods disclosed herein provide superior detection of osteoarthritis in comparison to conventional diagnostic testing. "Conventional methods to diagnose OA" are familiar to one of skill in the art and include X-ray, magnetic resonance imaging or the use of ultrasound. In particular aspects of the invention, the accuracy of the present methods are equal to or greater than that of conventional radiological or magnetic resonance testing used to detect the presence of OA.

The biomarkers of the present invention include genes and proteins, and variants and fragments thereof. Such biomarkers include polynucleotides, e.g, DNA comprising the entire or partial sequence of the nucleic acid sequence encoding the biomarker, or the complement of such a sequence. Biomarker polynucleotides may also include RNA comprising the entire or partial sequence of any of the nucleic acid sequences of interest. A biomarker protein is a protein encoded by or corresponding to a DNA biomarker of the invention. A biomarker protein comprises the entire or partial amino acid sequence of any of the biomarker proteins or polypeptides disclosed herein.

A "biomarker" is any gene or protein whose level of expression in a tissue or cell is altered compared to that of a normal or healthy cell or tissue. Biomarkers of the present invention are differentially expressed in felines with osteoarthritis. By "differentially expressed in osteoarthritis" is intended that the gene expression levels of the biomarkers of interest are either up or down regulated in a subject having, or predisposed to having, osteoarthritis compared to levels in a control subject. i.e., a subject not having or predisposed to having the condition. It is contemplated herein that detection of the biomarkers of the invention not only permits the identification of a subject having OA, but may also provide a means to identify an animal predisposed to developing this condition, ideally before physical symptoms manifest. If possible, such early detection would allow for improved patient care and could possibly prevent disease associated irreversible joint damage.

In some embodiments, the methods for diagnosing osteoarthritis disclosed herein may be performed as a primary means to screen for osteoarthritis in a feline. Said feline may be screened as part of a routine physical evaluation. A feline may also be screened according to the methods of the present invention because information indicates that the feline may be genetically predisposed to OA based on the medical history of its dam and/or sire, or because the feline is suspected to have the condition based on observed changes in behavior patterns. The methods of the present invention may also be used as part of a clinical examination in conjunction with conventional methods for diagnosing OA in a feline, e.g. X-ray or MRI, when said conventional methods are inconclusive or when confirmation of a diagnosis based on conventional techniques is desired.

The biomarkers of the invention include any polynucleotide or protein that is selectively differentially expressed in osteoarthritis, as defined herein above. Although any biomarker indicative of osteoarthritis may be used in the present invention, in certain embodiments the biomarkers include any one or more, or subsets of biomarkers set forth herein on FIGS. 1-2C.

Although the methods of the invention require the detection of at least one biomarker in a patient sample for the detection of osteoarthritis, it is contemplated herein that several or more biomarkers may be used to practice the present invention. Therefore, in some embodiments, one or more biomarkers are used, more preferably, two or more complementary biomarkers. By "complementary" is intended that detection of the combination of biomarkers in a body sample results in the successful identification of osteoarthritis in a greater percentage of cases than would be identified if only one of the biomarkers was used. Thus, in some cases, a more accurate determination of osteoarthritis can be made by using at least two biomarkers. Accordingly, where at least two biomarkers are used, at least two antibodies directed to distinct biomarker proteins can be used to practice the diagnostic methods disclosed herein. For example, antibodies or nucleic acid probes may be contacted with a body sample simultaneously or concurrently.

In particular embodiments, the diagnostic methods of the invention comprise collecting a blood sample from a feline patient, contacting the sample with at least one antibody specific for a biomarker of interest, and detecting antibody binding. Samples that exhibit differential expression of a biomarker of the invention, as determined by detection of antibody binding, are deemed positive for osteoarthritis. In particular embodiments, the body sample is a blood sample obtained from a feline by conventional methods such as density gradient separation methods, e.g., Ficoll-hypaque technique, or using cell preparation tubes (CPT™ tubes) from Becton Dickinson or other methods familiar to one of skill in the art.

By "body sample" is intended any sampling of cells, tissues, or bodily fluids in which expression of a biomarker can be detected. Examples of such body samples include, but are not limited to, blood, lymph, urine, biopsies, and smears. Body samples may be obtained from a feline by a variety of techniques including, for example, by scraping or swabbing an area or by using a needle to aspirate bodily fluids. Methods for collecting various body samples are well known in the art. In particular embodiments, the body sample comprises blood cells.

Any methods available in the art for identification or detection of the OA biomarkers of the present invention are encompassed herein. The differential expression of a biomarker of the invention can be detected on a nucleic acid level or a protein level. As described above, in order to determine differential expression, the body sample to be examined may be compared with a corresponding body sample that originates from a healthy subject. That is, the "normal" level of expression is the level of expression of the biomarker in the cells of a subject feline not afflicted with or predisposed to osteoarthritis. In some cases where the ratio of expression of a biomarker in an arthritic animal compared to a control is known, differential expression of said biomarker may be characterized in an animal without direct comparison to a normal.

Methods for detecting biomarkers of the invention comprise any methods that determine the quantity or the presence of the biomarkers either at the nucleic acid or protein level. Such methods are well known in the art and include but are not limited to Western blots, Northern blots, Southern blots, ELISA, immunoprecipitation, immunofluorescence, flow cytometry, immunocytochemistry, nucleic acid hybridization techniques, nucleic acid reverse transcription methods, and nucleic acid amplification methods. In particular embodiments, differential expression of a biomarker is detected on a protein level using, for example, antibodies that are directed against specific biomarker proteins. These antibodies can be used in various methods such as Western blot, ELISA, immunoprecipitation, or immunocytochemistry techniques. In addition, data from conventional diagnostic imaging using X-ray, or magnetic resonance may be obtained and compared to the immunocytochemical or nucleic acid probe hybridization information. In this manner, the detection of the biomarkers can confirm results from conventional diagnostic methods or provide clarity when data from conventional methods are inconclusive.

In one embodiment, antibodies specific for biomarker proteins are utilized to detect the differential expression of a biomarker protein in a body sample. The method comprises obtaining a body sample from a subject, contacting the body sample with at least one antibody directed to a biomarker that is selectively differentially expressed in osteoarthritis, and detecting antibody binding to determine if the biomarker is similarly differentially expressed in the sample. A preferred aspect of the present invention provides an immunocytochemistry technique for diagnosing osteoarthritis using a blood sample from a subject.

In a preferred immunocytochemical method, a blood sample is collected from a subject using methods familiar to one of skill in the art. For example, as described in the examples provided herein. PAXgene blood RNA tubes (for use in PAX gene blood RNA isolation) may also he employed where isolation of nucleic acid is desired. The blood sample may be assayed immediately or stored under appropriate conditions familiar to one of skill in the art for later analysis.

Alternatively, an antibody, particularly a monoclonal antibody, directed to a biomarker of interest may be incubated with a blood sample from a subject. As noted above, one of skill in the art will appreciate that a more accurate diagnosis of osteoarthritis may be obtained in some cases by detecting more than one biomarker in a patient sample. Therefore, in particular embodiments, at least two antibodies directed to two distinct biomarkers are used to detect osteoarthritis. Where more than one antibody is used, these antibodies may be added to a single sample sequentially as individual antibody reagents or simultaneously as an antibody cocktail. Alternatively, each individual antibody may be added to a separate sample from the same patient, and the resulting data pooled. In particular embodiments, an antibody cocktail may comprises several antibodies, wherein said antibodies bind to, e.g., a subset of the OA biomarkers disclosed in FIGS. 1-2C.

The terms "antibody" and "antibodies" broadly encompass naturally occurring forms of antibodies and recombinant antibodies such as single-chain antibodies, chimeric and humanized antibodies and multi-specific antibodies as well as fragments and derivatives of all of the foregoing, which fragments and derivatives have at least an antigenic binding site. Fully assembled antibodies and antibody fragments that can bind antigen are included in this definition. Antibody derivatives may comprise a protein or chemical moiety conjugated to the antibody.

"Antibody fragments" comprise a portion of an intact antibody, preferably the antigen-binding or variable region of the intact antibody. Examples of antibody fragments include Fab, Fab', F(ab')$_2$, and Fv fragments: diabodies; linear antibodies (Zapata et al. (1995) Protein Eng. 8(10):1057 1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment. Pepsin treatment yields an F(ab')$_2$ fragment that has two antigen-combining sites and is still capable of cross-linking antigen. Described herein are methods for the production of antibodies capable of specifically recognizing one or more differentially expressed gene epitopes. Such antibodies may include, but are not limited to, polyclonal antibodies, monoclonal antibodies (mAbs), humanized or chimeric antibodies, single chain antibodies. Fab fragments, F(ab')$_2$ fragments. fragments produced by a Fab expression library, anti-idiotypic (anti-Id) antibodies, and epitope-binding fragments of any of the above.

For the production of antibodies to a differentially expressed gene, various host animals may be immunized by injection with a differentially expressed gene protein, or a portion thereof. Such host animals may include but are not limited to rabbits, mice, rats, and chickens to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Polyclonal antibodies are heterogeneous populations of antibody molecules derived from the sera of animals immunized with an antigen, such as target gene product, or an antigenic functional derivative thereof. For the production of polyclonal antibodies, host animals such as those described above may be immunized by injection with differentially expressed gene product, supplemented with adjuvants as also described above.

Monoclonal antibodies, which are homogeneous populations of antibodies to a particular antigen, may be obtained by any technique that provides for the production of antibody molecules by continuous cell lines in culture. These include, but are not limited to the hybridoma technique of Kohler and Milstein, (1975, Nature 256:495-497: and U.S. Pat. No. 4,376,110), the human B-cell hybridoma technique (Kosbor et al., 1983, Immunology Today 4:72: Cole et al., 1983, Proc. Natl. Acad. Sci. USA 80:2026-2030), and the EBV-hybridoma technique (Cole et al., 1985, Monoclonal Antibodies And Cancer Therapy, Alan R. Liss, Inc., pp. 77-96). Such antibodies may be of any immunoglobulin class including IgG, IgM, IgE, IgA, IgD and any subclass thereof. The hybridoma producing the mAb of this invention may be cultivated in vitro or in vivo.

In addition, techniques developed for the production of "chimeric antibodies" (Morrison et al., 1984, Proc. Natl. Acad. Sci., 81:6851-6855: Neuberger et al., 1984. Nature, 312:604-608; Takeda et al., 1985, Nature. 314:452-454) by splicing the genes from a mouse antibody molecule of appropriate antigen specificity together with genes from a human antibody molecule of appropriate biological activity, can be used. A chimeric antibody is a molecule in which different portions are derived from different animal species, such as those having a variable or hypervariable region derived from a murine mAb and a human immunoglobulin constant region.

Alternatively, techniques described for the production of single chain antibodies (U.S. Pat. No. 4,946,778: Bird, 1988, Science 242:423-426: Huston et al., 1988, Proc. Natl. Acad.

Sci. USA 85:5879-5883; and Ward et al., 1989, Nature 334: 544-546) can be adapted to produce differentially expressed gene-single chain antibodies. Single chain antibodies are formed by linking the heavy and light chain fragments of the Fv region via an amino acid bridge, resulting in a single chain polypeptide.

Most preferably, techniques useful for the production of "humanized antibodies" can be adapted to produce antibodies to the polypeptides, fragments, derivatives, and functional equivalents disclosed herein. Such techniques are well known to those of skill in the art and are disclosed in. e.g., U.S. Pat. Nos. 5,932,448: 5.693,762: 5,693,761; 5,585,089; 5,530,101; 5,910,771: 5,569,825; 5.625.126: 5,633,425; 5.789,650; 5,545,580: 5,661.016; and 5,770,429, the disclosures of all of which are incorporated by reference herein in their entirety.

Antibody fragments which recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275-1281) to allow rapid and easy identification of monoclonal Fab fragments with the desired specificity. Particularly preferred, for ease of detection, is the sandwich assay, of which a number of variations exist, all of which may be employed in the methods of the present invention. Specifically, Elisa methods, including standard, sandwich and microformat Elisa methodologies familiar to one of skill in the art, may be used.

In some cases, an unlabeled antibody is immobilized on a solid substrate and the sample to be tested brought into contact with the bound molecule. After a suitable period of incubation, for a period of time sufficient to allow formation of an antibody-antigen binary complex, a second antibody, labeled with a reporter molecule capable of inducing a detectable signal, is then added and incubated, allowing time sufficient for the formation of a ternary complex of antibody-antigen-labeled antibody. Any unreacted material is washed away, and the presence of the antigen is determined by observation of a signal, or may be quantitated by comparing with a control sample containing known amounts of antigen. Variations include a simultaneous assay, in which both sample and antibody are added simultaneously to the bound antibody, or an assay in which the labeled antibody and sample to be tested are first combined, incubated and added to the unlabeled surface bound antibody. These techniques are well known to those skilled in the art, and the possibility of minor variations will be readily apparent.

The most commonly used reporter molecules in this type of assay are either enzymes, fluorophore- or radionuclide-containing molecules. In the case of an enzyme immunoassay, an enzyme is conjugated to the second antibody, usually by means of glutaraldehyde or periodate. As will be readily recognized, however, a wide variety of different ligation techniques exist, which ae well-known to the skilled artisan. Commonly used enzymes include horseradish peroxidase, glucose oxidase, beta-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or toluidine are commonly used. It is also possible to employ fluorogenic substrates, which yield a fluorescent product rather than the chromogenic substrates noted above. Spectophotometric methods may also be used to evaluate the presence of antigen in the serum sample.

Alternately, fluorescent compounds, such as fluorescein and rhodamine, may be chemically coupled to antibodies without altering their binding capacity. When activated by illumination with light of a particular wavelength, the fluorochrome-labeled antibody absorbs the light energy, inducing a state of excitability in the molecule, followed by emission of the light at a characteristic longer wavelength. The emission appears as a characteristic color visually detectable with a light microscope. Immunofluorescence and EIA techniques are both very well established in the art and are particularly preferred for the present method. However, other reporter molecules, such as radioisotopes, chemiluminescent or bioluminescent molecules may also be employed. It will be readily apparent to the skilled artisan how to vary the procedure to suit the required use.

With regard to detection of antibody staining in the immunocytochemistry methods of the invention, there also exist in the art video-microscopy and software methods for the quantitative determination of an amount of multiple molecular species (e.g., biomarker proteins) in a biological sample wherein each molecular species present is indicated by a representative dye marker having a specific color. Such methods are also known in the art as calorimetric analysis methods. In these methods, video-microscopy is used to provide an image of the biological sample after it has been stained to visually indicate the presence of a particular biomarker of interest. Some of these methods, such as those disclosed in U.S. Pat. No. 7,065,236, incorporated herein by reference, disclose the use of an imaging system and associated software to determine the relative amounts of each molecular species present based on the presence of representative color dye markers as indicated by those color dye markers' optical density or transmittance value, respectively, as determined by an imaging system and associated software. These techniques provide quantitative determinations of the relative amounts of each molecular species in a stained biological sample using a single video image that is "deconstructed" into its component color parts.

The antibodies used to practice the invention are selected to have high specificity for the biomarker proteins of interest. While methods for making antibodies and for selecting appropriate antibodies are known in the art and described above, it is also contemplated herein that in some embodiments, commercial antibodies directed to specific biomarker proteins may be used to practice the invention.

One of skill in the art will recognize that the concentration of a particular antibody used to practice the methods of the invention may vary depending on such factors as time for binding, level of specificity of the antibody for the biomarker protein, and method of body sample preparation. Moreover, when multiple antibodies are used, the required concentration may be affected by the order in which the antibodies are applied to the sample, i.e., simultaneously as a cocktail, or sequentially as individual antibody reagents. Furthermore, the detection chemistry used to visualize antibody binding to a biomarker of interest must also be optimized to produce the desired signal to noise ratio.

In other embodiments, the expression of a biomarker of interest is detected at the nucleic acid level. Nucleic acid-based techniques for assessing expression are well known in the art and include, for example, determining the level of biomarker mRNA in a body sample. Many expression detection methods use isolated RNA. As used herein, "RNA" includes total RNA as well as mRNA. Any RNA isolation technique that does not select against the isolation of mRNA can be utilized for the purification of RNA from blood cells (see, e.g., Ausubel et al., ed., (1987 1999) Current Protocols in Molecular Biology (John Wiley & Sons. New York). Additionally, large numbers of tissue samples can readily be processed using techniques well known to those of skill in the art. such as, described in U.S. Pat. No. 4,843.155.

The term "probe" refers to any molecule that is capable of selectively binding to a specifically intended target biomolecule, for example, a nucleotide transcript or a protein encoded by or corresponding to an OA biomarker. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or Northern analyses, polymerase chain reaction analyses and probe arrays. One method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof such as an oligonucleotide of at least 7, 15, 30, 50, 100, 250 or 500 nucleotides in length and sufficient to specifically hybridize under stringent conditions to an mRNA or genomic DNA encoding a biomarker of the present invention. Hybridization of an mRNA with the probe indicates that the biomarker in question is being expressed.

In one embodiment, the mRNA is immobilized on a solid surface and contacted with a probe, for example by running the isolated mRNA on an agarose gel and transferring the mRNA from the gel to a membrane, such as nitrocellulose. A skilled artisan can readily adapt known mRNA detection methods for use in detecting the level of mRNA encoded by the biomarkers of the present invention.

In an alternative embodiment, the probe(s) for an OA biomarker are immobilized on a solid surface and the mRNA is contacted with the probe(s). As contemplated herein, gene chips, (e.g., high density oligonucleotide arrays), microarrays (e.g., cDNA arrays or oligonucleotide arrays printed on glass slides), macroarrays, (e.g., PVDF membranes on which genes are printed) and bead-based arrays (e.g. Illumina bead based microarrays) are among the possible assay platforms that may be used in the methods of the present invention. Thus, in one embodiment of the invention, microarrays are used to detect biomarker expression, and such methods are useful to detect expression levels of a number of different genes. Microarray technologies, e.g., such as commercially available from Affymetrix, are familiar to one of skill in the art. It is contemplated herein that microarrays or "chips" designed for the detection of expression of the OA biomarkers disclosed herein may be created for use in the methods of the present invention. As used herein, "microarray" is meant to include all array platform technologies, which may include, e.g., gene chips, or bead arrays, and may include peptides or nucleic acids, e.g., RNA, DNA, cDNA, PCR products or ESTs, on beads, gels, polymeric surfaces, fibers such as fiber optics, glass or any other appropriate substrate.

An alternative method for determining the level of biomarker mRNA in a sample involves the process of nucleic acid or oligonucleotide amplification, e.g., by RT-PCR, including quantitative or qRT-PCR, ligase chain reaction (Barany (1991) Proc. Natl. Acad. Sci. USA 88:189 193), self sustained sequence replication (Guatelli et al. (1990) Proc. Natl. Acad. Sci. USA 87:1874 1878). transcriptional amplification system (Kwoh et al. (1989) Proc. Natl. Acad. Sci. USA 86:1173 1177). Q-Beta Replicase (Lizardi et al. (1988) Bio/Technology 6:1197), rolling circle replication or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention. biomarker expression is assessed by quantitative RT-PCR.

Biomarker expression levels of RNA may be monitored using conventional methods, e.g. a membrane blot (such as used in hybridization analysis such as Northern, Southern. dot, and the like), or microwells, sample tubes, gels, beads or fibers (or any solid support comprising bound nucleic acids). The detection of biomarker expression may also comprise using nucleic acid probes in solution.

Kits for practicing the methods of the invention are also contemplated herein. By "kit" is intended any manufacture (e.g., a package or a container) comprising the components necessary to detect differential expression of an OA biomarker in a feline. Said kits may comprise, for example, at least one reagent. e.g., an antibody, a nucleic acid probe, etc. for specifically detecting the expression of a biomarker of the present invention. As contemplated herein, the kits of the present invention may focus on the diagnostic use of a single type of component (for example, reagents such as antibodies or nucleic acid probes) or may comprise different types of components and the relative amounts of each may vary, such that the majority of the components may be of one type or another, or the reagents may be of equal amounts. A kit of the present invention may also comprise a microarray comprising one or more nucleic acids specific for the OA biomarkers of the present invention or subsets of said biomarkers. The kit may be promoted, distributed, or sold as a unit for performing the methods of the present invention. Additionally, the kits may contain a package insert describing the kit and methods for its use.

In a particular embodiment, kits for practicing the immunocytochemistry methods of the invention are provided. Such kits are compatible with both manual and automated immunocytochemistry techniques (e.g., cell staining). These kits comprise at least one antibody directed to a biomarker of interest, chemicals for the detection of antibody binding to the biomarker, and a counterstain. Any chemicals that detect antigen-antibody binding may be used in the practice of the invention. In some embodiments, the detection chemicals comprise a labeled polymer conjugated to a secondary antibody. For example, a secondary antibody that is conjugated to an enzyme that catalyzes the deposition of a chromogen at the antigen-antibody binding site may be provided. Such enzymes and techniques for using them in the detection of antibody binding are well known in the art.

In another embodiment, the kits of the invention additionally comprise at least two or more reagents, e.g., antibodies, for specifically detecting the expression of at least two or more distinct biomarkers. Each antibody may be provided in the kit as an individual reagent or, alternatively, as an antibody cocktail comprising all of the antibodies directed to the different biomarkers of interest. Furthermore, any or all of the kit reagents may be provided within containers that protect them from the external environment, such as in sealed containers.

Positive and/or negative controls may be included in the kits to validate the activity and correct usage of reagents employed in accordance with the invention. Controls may include samples, such as tissue sections, cells fixed on glass slides, etc., known to be either positive or negative for the presence of the biomarker of interest. The design and use of controls is standard and well within the routine capabilities of those of ordinary skill in the art.

In other embodiments, kits for identifying OA in a feline comprising detecting differential expression of a biomarker at the nucleic acid level are provided. Such kits comprise, for example, at least one nucleic acid probe that specifically binds to a biomarker nucleic acid or fragment thereof. In particular embodiments, the kits comprise at least two or more nucleic acid probes that hybridize with distinct biomarker nucleic acids and may additionally comprise a microarray comprising nucleic acid encoding the OA biomarkers.

It is contemplated that the invention described herein is not limited to the particular methodology, protocols, and reagents described as these may vary. It is also to be understood that the terminology used herein is for the purpose of describing particular embodiments only, and is not intended to limit the scope of the present invention in any way.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices and materials are now described. All publications mentioned herein are incorporated by reference for the purpose of describing and disclosing the materials and methodologies that are reported in the publication which might be used in connection with the invention.

In practicing the present invention, many conventional techniques in molecular biology may be used. These techniques are well known and are explained in, for example, Current Protocols in Molecular Biology, Volumes I. II, and III. 1997 (F. M. Ausubel ed.); Sambrook et al., 1989, Molecular Cloning: A Laboratory Manual, Second Edition, Cold Spring Harbor Laboratory Press. Cold Spring Harbor, N.Y.

As used herein and in the appended claims, the singular forms "a", "an" and "the" include plural reference unless the context clearly dictates otherwise. Thus, for example, reference to the "antibody" is a reference to one or more antibodies and equivalents thereof known to those skilled in the art, and so forth.

The following examples are offered by way of illustration and not by way of limitation.

EXAMPLES

Example 1

Gene Expression in Cats with Osteoarthritis Compared to Control Cats

Studies are conducted using non-arthritic cats and cats with osteoarthritis (OA) to determine the underlying gene expression differences between non-arthritic cats and cats with OA. In one study, a baseline comparison is performed between the two groups to determine the underlying gene expression differences between non-arthritic cats and cats with OA. In a second study, another group of non-arthritic cats and cats with OA are used, however, in addition to the baseline comparison between all normal animals and all OA animals, a diet is tested over time for the ability to dampen the progression of the disease. Quantitative real-time PCR studies are also performed using the samples obtained from the second study.

With regard to the studies provided herein, cats with OA are graded according to a previously published method, i.e., all non-arthritic cats are "grade 0" indicating that the joint appears to be normal, cats with OA have grades that are either 1 (small enthesophytes or small osteophytes present) or 2 (more prominent enthesophytes and osteophytes). Cats with severe OA (grade 3) are not included in this study.

Whole blood is obtained from the cats in the studies provided herein using PAXgene™ RNA tubes and total RNA is isolated from whole blood samples using PAXgene™ RNA isolation kit according to the methods detailed below.

PAXgene™ Blood RNA Isolation: PAXgene™ Blood RNA tubes and the PAXgene™ Blood RNA Kit (Qiagen) are used together to isolate and purify intracellular RNA from whole blood obtained from felines as provided below (see also PAXgene™ Blood RNA Kit Handbook, PreAnalytix, June 2005). Briefly, blood is collected using a Vacutainer® needle, directly into the PAXgene™ Blood RNA tube and then subjected to several rounds of centrifugation, wash and purification steps which ultimately result in high-quality RNA. The RNA then undergoes a quality control step and is then used in future quantitative real-time PCR and/or microarray analyses using a custom manufactured proprietary feline gene chip produced on the Affymetrix platform.

Assay Preparations: Incubate PAXgene™ tubes (containing blood) for at minimum of 2 hours at room temperature before beginning the assay. If the tubes are frozen, and are not allowed to incubate for 2 hours prior to freezing, they will need to sit at room temperature to thaw an additional 2 hours. Invert each PAXgene™ tube 8-10 times before the first centrifugation. If using Buffer BR4 (buffers are included with the PAXgene™ Blood RNA Kit) for the first time, add 4 volumes of 96-100% ethanol to the concentrated buffer to obtain a working solution. Preheat two heating blocks prior to beginning the assay—65° C. and 55° C. Prepare the DNase I stock solution (the RNase-Free DNase Set is included with the PAXgene™ Blood RNA Kit). Dissolve the solid DNase I enzyme in 550 µL of RNase-free water provided with the kit. Be sure not to lose any DNase I when removing the lid. Mix gently by inverting the tube. Do not vortex or centrifuge. Make a mixture of DNase I enzyme and Buffer RDD (kit component) (enough volume for the number of samples being processed per hatch). Each sample needs 704, of Buffer RDD and 104 of DNase I (i.e. 20 samples would require a cocktail of 1.4 mL Buffer RDD and 200 µl, DNase I). The cocktail should he stored at 2-8° C. until needed. The reconstituted enzyme is good for up to 6 weeks at 2-8° C.

Sample storage: PAXgene™ tubes (which contain blood) can be stored at room temperature for up to 3 days before processing. According to the product insert provided with the PAXgene™ Blood RNA tubes, the cellular RNA profile is stable under these conditions for up to 3 days. This, however, may vary between species. PAXgene™ tubes can also be stored at 4° C. for up to 5 days. If long term storage is required, PAXgene™ tubes can be stored at -20° C. or -70° C. for up to 6 months. Tubes should be frozen in a loose wire rack in an upright position. It is recommended to freeze first at -20° C. and then transfer to -70° C. if tubes will be stored at -70° C. Upon removing the tubes from the freezer they should be thawed at room temperature (temperature not to exceed 22° C.). Each tube is to be inverted 10 times before proceeding with the assay.

RNA Isolation from Whole Blood: Centrifuge the PAXgene™ Blood RNA tubes at 4000×g for 10 minutes. Remove the supernatant by decanting and discard. Blot excess supernatant remaining on rim of PAXgene™ tube. Add 4 mL of RNase-free water to the pellet and cap with a new Hemogard closure. Resuspend the pellet by vortexing and then centrifuge at 4000×g for 10 minutes. Remove the supernatant by decanting and discard. Blot excess supernatant remaining on rim of PAXgene™. Add 360 µL of Buffer BR1 (kit component) to the pellet and gently pipette until pellet is completely resuspended. Transfer the sample to a sterile 1.5 mL microcentrifuge tube and add 300 µL Buffer BR2 (kit component) and 40 µL Proteinase K (do not mix Buffer BR2 and Proteinase K prior to adding to the sample). Mix each tube thoroughly by vortexing and place into a thermomixer preheated to 55° C. Incubate/shake the tubes for 10 minutes at 1400 rpm. Pipet the lysate into a Q1A shredder spin column placed into a 2 mL collection tube. Centrifuge at 14,000 rpm for 3 minutes. Transfer the supernatant of the flow-through fraction to a sterile 1.5 mL microcentrifuge tube. Add 350 µL of 96-100% ethanol and gently mix by pipetting. Add 700 µL of the sample to the PAXgene™ spin column placed in a 2 mL collection tube and centrifuge at 14,000 rpm for 1 minute. Transfer the PAXgene™ spin column into a new 2 mL collection tube and discard the flow-through and old collection tube. Add the remaining volume of the sample to the PAXgene™ spin column. Centrifuge at 14,000 rpm for 1 minute.

Discard the old collection tube and the flow-through from the centrifugation of the spin column described immediately above. Place the PAXgene™ spin column into a new 2 mL collection tube. Add 350 µL of Buffer BR3 (kit component) to the PAXgene™ spin column and centrifuge at 14,000 rpm for 1 minute. Discard the flow-through and collection tube. Place the column into a new 2 mL collection tube and add 80 µL of the DNase I/Buffer RDD cocktail (see "Assay Preparations") directly to the column membrane and incubate for 15 minutes at room temperature. Add another 350 µL Buffer BR3 to the PAXgene™ spin column. Centrifuge at 14,000 rpm for 1 minute. Transfer the PAXgene™ spin column to a new 2 mL collection tube and discard the old collection tube and flow-through.

Add 500 µL of Buffer BR4 (kit component) to the PAXgene™ spin column. Centrifuge at 14,000 rpm for 1 minute. Place the PAXgene™ spin column into a new 2 mL collection tube and discard the old collection tube and flow-through. Add another 500 µL Buffer BR4 to the PAXgene™ spin column. Centrifuge at 14,000 rpm for 3 minutes to dry the spin column membrane. Discard the collection tube and flow-through and place the columns in another 2 mL collection tube. Spin the samples again at 14,000 rpm for an additional minute to further dry the column membrane. Discard the flow-through and the collection tube. Transfer the PAXgene™ spin column to a 1.5 mL elution tube. Add 404 Buffer BR5 (kit component) directly to the PAXgene™ spin column membrane. Centrifuge at 14,000 rpm for 1 minute. Remove the PAXgene™ spin column and pipette the eluate in the 1.5 mL tube onto the same PAXgene™ spin column. Return the PAXgene™ spin column to the same 1.5 mL elution tube and centrifuge at 14,000 rpm for 1 minute. Incubate the final eluate at 65° C. for 5 minutes and immediately chill on ice. Store final RNA sample at −80° C. for future use.

Example 2

Gene Chip Analyses

A proprietary, custom made feline gene chip (Affymetrix) is used to evaluate base line gene expression in cats with and without OA (10 normals, 10 arthritic animals). As provided above, gene chip analyses are performed using conventional methods and according to the manufacturer's instructions in order to obtain a baseline comparison between the two groups to determine the underlying gene expression differences between non-arthritic cats and cats with OA.

The raw gene chip data is normalized using the Robust Multiarray Average (RMA) normalization algorithm (Irizarry. et al., Biostatistics 2003 Vol 4, Page 249-264) and is then subjected to statistical analysis using Support Vector Machine (SVM) algorithm (Partek Genomic Suite, Version 6) to determine the gene expression differences that can differentiate between arthritic and non-arthritic animals. Genes identifying OA biomarkers are selected based on p value cut off and fold change (FC) according to the following: genes with p value <0.001 and displaying a fold change of either >2.0 or >1.5. The lists of feline OA biomarkers thus identified are provided herein in FIGS. 1-2C.

The results from these studies indicate that gene expression can be used to differentiate between normal cats and cats with OA. The lists of differentially expressed genes include sequences that act as cell surface markers, receptors and other signaling molecules.

Example 3

Effect of Diet on Gene Expression in Feline Arthritis

In this study, quantitative real-time PCR assays are performed using RNA isolated from normal and arthritic cats. In addition to a baseline comparison between arthritic and normal animals, the effect of diet is also measured. Specifically, following standard animal nutrition testing procedures familiar to one of skill in the art, arthritic and normal cats are fed test diets comprising components reported to be of use to combat inflammatory disease, including polyunsaturated fatty acids such as omega-3 fatty acids, such as provided in WO 2007/002837 A2 ("j/d") and WO 2006/074089 A2 ("senior") and then changes in gene expression in the animals is analyzed using qRT-PCR. OA serum markers are also assayed using conventional methods (ELISA).

With regard to q RT-PCR, Taqman probe technology is used and all analyses are carried out using an Applied Biosystems 7500 real-time PCR machine. The data is analyzed using the sequence detection software package version 1.2.2. provided by the manufacturer.

A baseline comparison of normal and arthritic animals using qRT-PCR detect OA biomarker genes associated with proteases and cartilage degradation: Caspase 1, Caspase 3, MMP 2, MMP16. Inhibitor of MMP1. Inhibitor of MMP2, Inhibitor of MMP3, Cysteine protease. PUMP-1 and Progesterone-dependent protein and genes associated with inflammation: IFN-gamma; TGF-beta; MIP-1 alpha; IL-1 alpha; IL-1 beta; IL-2; IL-6 and IL-10. Data also indicate that IL-1 and TGF-beta are significantly different between the arthritic and nonarthritic animals. IL-1 is known to induce arthritic lesions in experimental animals. This result is corroborated by the gene chip analysis (data not shown).

Also, using conventional ELISA methods. blood levels of a peptide of type I collagen (NTx) and Collagen II (CTX-II) are measured in the animals and data indicate that cats fed a diet containing high levels of EPA and DHA show a marked reduction in circulating levels of these OA markers.

Clinical data obtained from nutritional studies involving the arthritic and non-arthritic animals described above indicate that dietary intervention can affect the expression of some OA biomarkers. Specifically, diets containing high levels of n-3 fatty acids DHA (0.3%) or DHA and EPA (0.3% and 0.46% respectively), can cause a decrease in the OA serum markers, collagen I (NTx) and a fragment of collagen II (CTX-II) but do not have an effect on levels of TGF-beta. With regard to TGF-beta, a lack of change which would be desired as this protein may play a protective role in arthritis. Furthermore, quantitative real-time PCR analysis reveals that the expression of IL-1 is also dramatically decreased in animals administered a diet containing DHA and EPA and this is desired as this protein is a known arthrogenic molecule. Thus, it is shown that feeding a diet rich in n-3 fatty acids EPA and DHA (based on TG oil) can cause a reduction in expression of IL-1. Nix and CTX-II.

What is claimed is:

1. A method for diagnosing osteoarthritis (OA) in a feline comprising:
   (a) determining the level of a protein product of Felis catus Toll-like receptor-2 in a body sample from said feline; and
   (b) comparing the level of said protein product of Felis catus Toll-like receptor-2 in the body sample from said feline with the levels in a control feline without OA, wherein differential expression of the protein product of Felis catus Toll-like receptor-2 between the individual and the control is indicative of OA in the feline.

2. The method according to claim 1 wherein the level of protein product of Felis catus Toll-like receptor-2 is determined using antibodies or fragments thereof.

3. The method according to claim 2, wherein the antibodies are monoclonal antibodies.

4. The method of claim 1 wherein said body sample is a blood sample.

5. The method of claim 1 wherein the method is performed in an automated manner.

6. The method of claim 1 wherein the method is performed in conjunction with the use of conventional methods to diagnose osteoarthritis in a feline.

7. The method of claim 1 wherein the method is performed as a primary means to diagnose osteoarthritis in a feline.

8. A method for diagnosing OA in a feline comprising:
   (a) determining the level of a protein product of Felis catus TCR alpha constant chain in a body sample from said feline; and
   (b) comparing the level of said protein product of Felis catus TCR alpha constant chain in the body sample from said feline with the levels in a control feline without OA, wherein differential expression of the protein product of Felis catus TCR alpha constant chain between the individual and the control is indicative of OA in the feline.

9. The method according to claim 8 wherein the level of protein product of Felis catus TCR alpha constant chain is determined using antibodies or fragments thereof.

10. The method according to claim 9, wherein the antibodies are monoclonal antibodies.

11. The method of claim 8 wherein said body sample is a blood sample.

12. The method of claim 8 wherein the method is performed in an automated manner.

13. The method of claim 8 wherein the method is performed in conjunction with the use of conventional methods to diagnose osteoarthritis in a feline.

14. The method of claim 8 wherein the method is performed as a primary means to diagnose osteoarthritis in a feline.

* * * * *